US00PP25728P2

(12) United States Plant Patent
Pounders et al.

(10) Patent No.: US PP25,728 P2
(45) Date of Patent: Jul. 21, 2015

(54) AZALEA PLANT NAMED 'AZ 15'

(50) Latin Name: *Rhododendron hybrida*
Varietal Denomination: AZ 15

(71) Applicants: The United States of America, as represented by the Secretary of Agriculture, Washington, DC (US); Capstone Plants Inc., Grand Saline, TX (US)

(72) Inventors: Cecil T Pounders, Poplarville, MS (US); James B Berry, Mineola, TX (US)

(73) Assignees: CAPSTONE PLANT, INC., Grand Saline, TX (US), part interest; THE UNITED STATES OF AMERICA AS REPRESENTED BY THE SECRETARY OF AGRICULTURE, Washington, DC (US), part interest ( * ) Notice: Subject to any disclaimer, the term of this patent is extended or adjusted under 35 U.S.C. 154(b) by 187 days.

(21) Appl. No.: 13/987,582

(22) Filed: Aug. 9, 2013

(51) Int. Cl.
*A01H 5/00* (2006.01)

(52) U.S. Cl.
USPC ..... Plt./240

(58) Field of Classification Search
None
See application file for complete search history.

*Primary Examiner* — Susan McCormick Ewoldt
(74) *Attorney, Agent, or Firm* — Penny J. Aguirre

(57) ABSTRACT

A new cultivar of hybrid Azalea named 'AZ 15' that is characterized by its repeat blooming habit, its bright red flowers with deeper red flecks on the upper surface of the petals, its mature foliage that is dark green and pest free with the new growth very pubescent, its strong and disease free root system, its stems and flower buds that are resistant to cold damage, its cold hardiness at least to U.S.D.A. Zone 7, and its ability to be readily propagated by softwood stem cuttings.

2 Drawing Sheets

Botanical classification: *Rhododendron hybrida.*
Cultivar designation: 'AZ 15'.

BACKGROUND OF THE INVENTION

The present invention relates to a new and distinct cultivar of *Rhododendron* plant of hybrid origin, botanically known as *Rhododendron hybrida* 'AZ 15' and will be referred to hereafter by its cultivar name, 'AZ 15'. 'AZ 15' is a new cultivar of evergreen Azalea grown for use as a landscape plant.

The new cultivar was developed through an on-going breeding program conducted by the Inventors in Poplarville, Miss. The objectives of the breeding program are to develop new cultivars of Azalea that exhibit tolerance to environmental stresses and disease resistance combined with unique flower colors and extended bloom periods.

The new cultivar arose from a cross made in 2005 between 'Friedhelm Scherr' (not patented) as the female parent and a plant selection from the Aromi group of hybrid Azaleas as the male parent (received unlabelled, none of the Aromi group of Azaleas have been patented). The Inventors selected 'AZ 15' as a single unique plant amongst the seedlings that resulted from the above cross in 2007.

Asexual propagation of the new cultivar was first accomplished by softwood stem cuttings in Poplarville, Miss. in 2008 by one of the Inventors. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics 'AZ 15'. These attributes in combination distinguish 'AZ 15' as a new and distinct cultivar of Azalea.

1. 'AZ 15' is a repeat bloomer with a strong bloom period in late March to early April followed by a seconding bloom period in late July through October in Mississippi.
2. 'AZ 15' exhibits bright red flowers with deeper red flecks on the upper surface of the petals.
3. 'AZ 15' exhibits mature foliage that is dark green and disease free with the new growth very pubescent; a trait that imparts resistance to insect feeding.
4. 'AZ 15' exhibits a compact plant habit with dense branching.
5. 'AZ 15' exhibits a strong and disease free root system.
6. 'AZ 15' exhibits a high tolerance to heat stress; thriving in summer temperatures that exceed 100° F. for 90 days or more.
7. 'AZ 15' exhibits stems and flower buds that are resistant to cold damage when exposed to temperatures down to 14° F.
8. 'AZ 15' is cold hardy at least to U.S.D.A. Zone 7.
9. 'AZ 15' is readily propagated by softwood stem cuttings under intermittent mist.

The female parent of 'AZ 15', 'Friedhelm Scherr', differs from 'AZ 15' in having much less cold hardiness and in having poor adaptation to heat and moisture stress. The male parent, a plant selection from the Aromi group of hybrid Azaleas, differs from 'AZ 15' in having a more robust growth habit and in being less floriferous. 'AZ 15' can also be most closely compared to the cultivars 'September Song' (not patented) and 'RLH1-1P2' (U.S. Plant Pat. No. 21,562). Both are similar to 'AZ 15' in flower color. 'September Song' differs from 'AZ 15' in having a more open growth habit, in being more difficult to propagate and in having a less vigorous root system. 'RLH1-1P2' differs from 'AZ 15' in having less heat tolerance, a slower growth rate, a greater susceptibility to petal blight and larger flowers.

BRIEF DESCRIPTION OF THE DRAWING

The accompanying colored photograph were taken of 18 month-old plants of the new cultivar as grown outdoors in three-gallon containers in a greenhouse in Grand Saline, Tex.

The photograph in FIG. 1 provides a view of 'AZ 15' in bloom.

Figure 1:
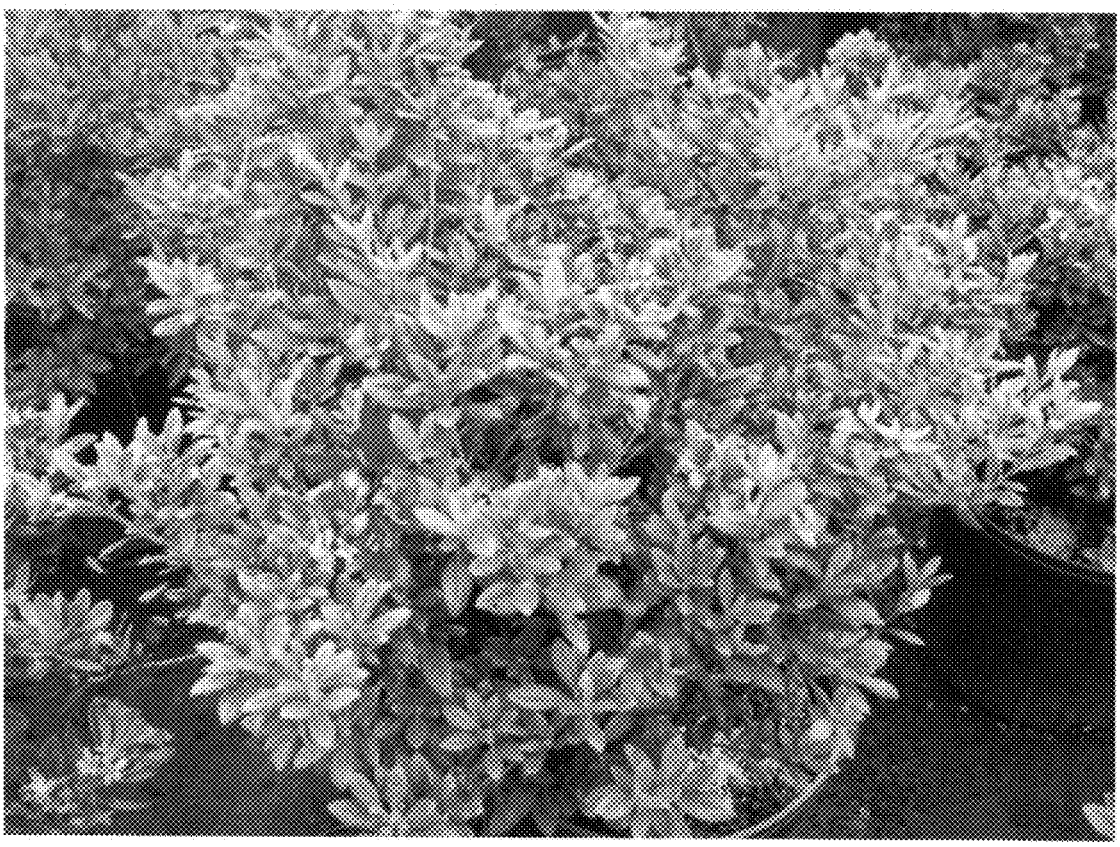
Figure 2:
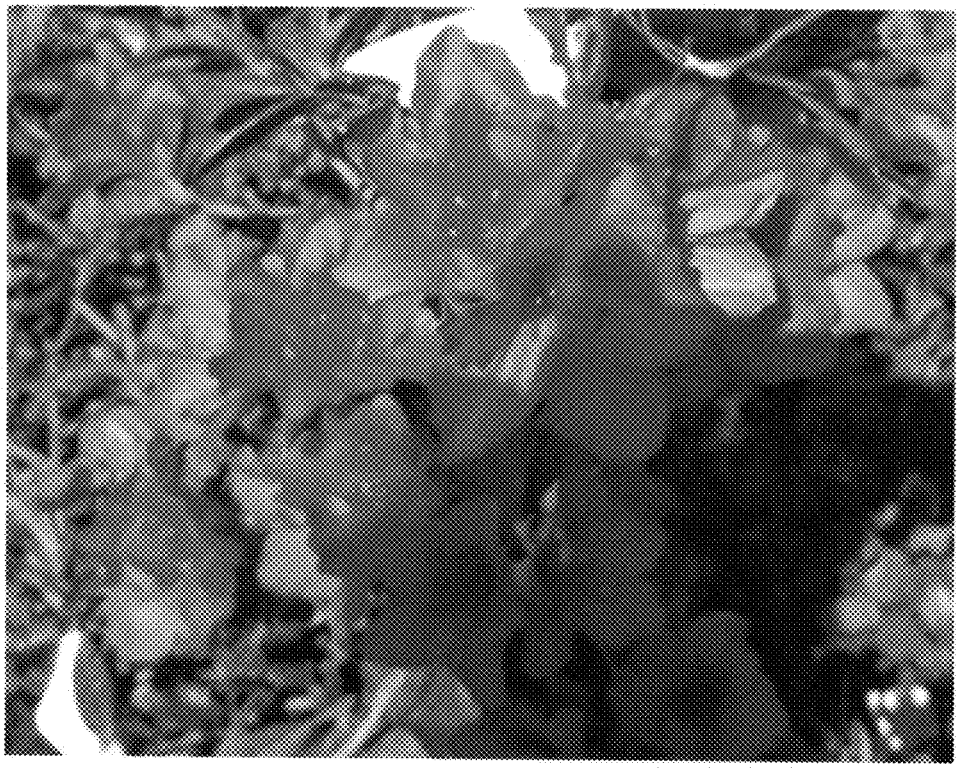

The photograph in FIG. 2 provides a close-up view of the inflorescences of 'AZ 15'.

Figure 3:
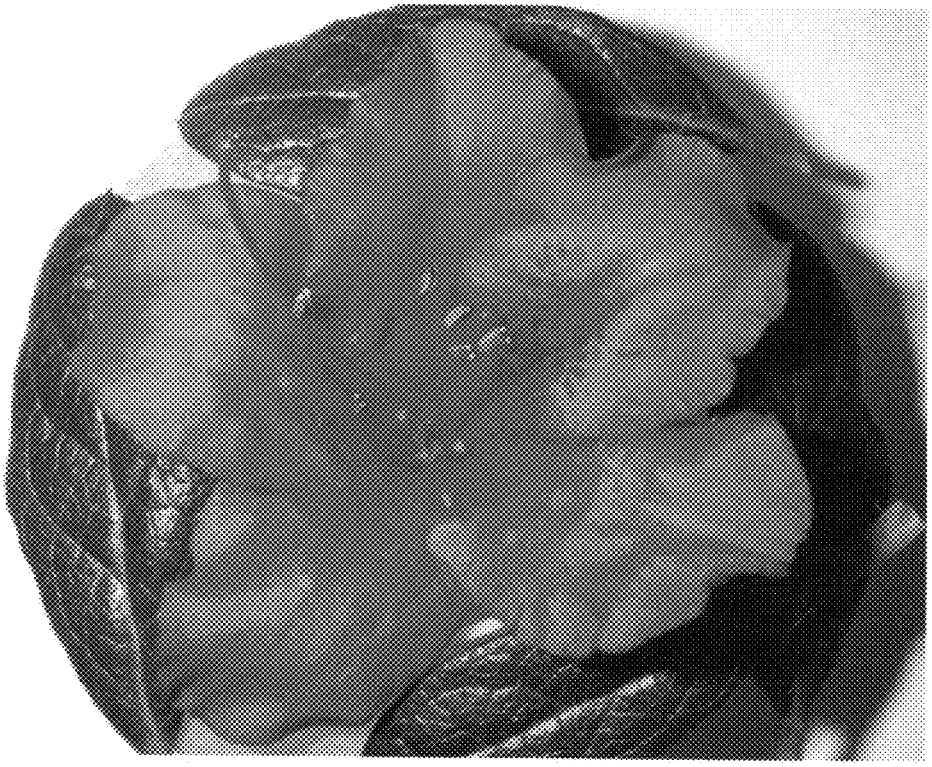

The photograph in FIG. 3 provides a close-up view of a flower and leaves placed on a mount.

The colors in the photographs are as close as possible with the digital photography and printing techniques utilized and the color codes in the detailed botanical description accurately describe the new Azalea.

DETAILED BOTANICAL DESCRIPTION OF THE PLANT

The following is a detailed description of 18 month-old plants of the new cultivar as grown outdoors in three-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Late March/early April and late July to October in Southern Mississippi, USA.

*Plant type.*—Evergreen shrub.

*Plant habit.*—Upright, compact, densely branched.

*Height and spread.*—Reaches 2 m in height and 3 m in spread.

*Cold hardiness.*—At least in U.S.D.A. Zones 7, stems and flower buds that are resistant to cold damage when exposed to temperatures down to 14° F.

*Diseases and pests.*—No disease problems have been observed, observed to have less insect feeding due to its highly pubescent new foliage.

*Root description.*—Abundant, fibrous, moderately dense.

*Propagation.*—Softwood stem terminal cuttings, readily propagated under intermittent mist.

*Growth rate.*—Vigorous.

Stem description:

*Shape.*—Round.

*Stem color.*—New growth; 145C, mature wood; 165A.

*Stem size.*—Main stems; an average of 16 cm in length and 1 cm in width, lateral stems; an average of 15 cm in length and 3 mm in diameter.

*Stem surface.*—New growth; very pubescent, mature wood; ridged bark, exfoliating.

*Stem aspect.*—Held at an average angle of 5 to 10° (0°=vertical).

*Stem strength.*—Strong.

*Branching.*—Self-branching, an average of 5 main stems and 8 lateral branches per main stem in a 3-gallon container.

*Internode.*—Average of 2 cm.

Foliage description:

*Leaf shape.*—Oblanceolate.

*Leaf division.*—Simple.

*Leaf base.*—Cuneate.

*Leaf apex.*—Acute with very tip mucronate.

*Leaf venation.*—Pinnate, upper and lower surface 151A in color, both surfaces moderately covered with stiff pubescence, upper surface pubescence NN155B, lower surface pubescence 46A in color.

*Leaf margins.*—Entire.

*Leaf attachment.*—Petiolate.

*Leaf arrangement.*—Alternate.

*Leaf orientation.*—Held horizontal to upright.

*Leaf aspect.*—Cupped downward.

*Leaf surface.*—Upper and lower surface coriaceous, cartilaginous, and shiny.

*Leaf color.*—Young leaves upper and lower surface; 145A, mature leaves upper surface; 133A, mature leaves lower surface; 146C.

*Leaf size.*—Average of 4 cm in length, and 15 cm in width.

*Leaf quantity.*—About 40 leaves per lateral branch 15 cm in length.

*Petioles.*—Average of 5 mm in length and 1 mm in diameter, 145B in color, sparsely pubescent surface.

Flower description:

*Inflorescence type.*—Flowers are solitary.

*Lastingness of flowers.*—About 10 days, self cleaning.

*Flower size.*—An average of 3 cm in depth and 4 cm in diameter.

*Flower fragrance.*—None.

*Flower shape.*—Tubular base with flared petal lobes.

*Flower number.*—Average of 3 per lateral stem.

*Flower aspect.*—Upright.

*Flower bud.*—Ovate in shape, an average of 15 mm in depth and 8 mm in diameter, apex; acute, color; 145B.

*Flower attachment.*—Pedicel.

*Petal number.*—5.

*Petal shape.*—Elliptic.

*Petal color.*—44A with internal freckles 53A in color on upper surface and 44A on lower surface.

*Petal surface.*—Both surfaces glabrous.

*Petal margins.*—Entire and slightly wavy.

*Petal apex.*—Acute.

*Petal base.*—Fused.

*Petal size.*—Average of 2.7 cm in length and 2 cm in width.

*Sepal number.*—5.

*Sepal shape.*—Lanceolate.

*Sepal margin.*—Entire.

*Sepal size.*—Average of 8 mm in length and 4 mm in width.

*Sepal aspect.*—Upright.

*Sepal surface.*—Pubescent on upper and lower surface.

*Sepal apex.*—Acute-slightly acuminate.

*Sepal base.*—Fused.

*Sepal color.*—Center 44C and edges 22D on upper and lower surface.

*Calyx.*—Campanulate in shape, average of 8 mm in length and 1.8 cm in diameter.

*Peduncles.*—An average of 7 mm in length and 2 mm in diameter, 44C in color, flexible strength, slightly pubescent surface, held upright.

*Pedicels.*—None.

Reproductive organs:

*Gynoecium.*—1 Pistil, stigmas; club-shaped, 44A in color, style; 4 cm in length and 44A in color, ovary; conical in shape, 4 mm in length and 3 mm in width, 155A in color due to heavy pubescence.

*Androecium.*—Stamens; average of 5, weak in strength, 2.5 cm in length, N74A in color, anthers; 187B in color; pollen sparse in quantity and N155A in color.

*Fruit/seeds.*—Seed pod an average of 12 mm in length and 5 mm in width, maturing from 133A to 199C in color.

It is claimed:

1. A new and distinct cultivar of Azalea plant named 'AZ 15' as herein illustrated and described.

* * * * *